US 12,084,478 B1

(12) United States Patent
Kandeel

(10) Patent No.: US 12,084,478 B1
(45) Date of Patent: *Sep. 10, 2024

(54) FUSION PEPTIDE INHIBITORS OF HUMAN CORONAVIRUS 229E

(71) Applicant: KING FAISAL UNIVERSITY, Al-Ahsa (SA)

(72) Inventor: Mahmoud Kandeel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,634

(22) Filed: Sep. 25, 2023

Related U.S. Application Data

(62) Division of application No. 18/198,100, filed on May 16, 2023, now Pat. No. 11,866,461.

(51) Int. Cl.
| | | |
|---|---|---|
| *A61K 38/16* | (2006.01) | |
| *A61K 39/215* | (2006.01) | |
| *A61P 31/14* | (2006.01) | |
| *C07K 14/00* | (2006.01) | |
| *C07K 14/08* | (2006.01) | |

(52) U.S. Cl.
CPC ............ *C07K 14/001* (2013.01); *A61P 31/14* (2018.01); *C07K 2319/00* (2013.01)

(58) Field of Classification Search
None
See application file for complete search history.

(56) References Cited

U.S. PATENT DOCUMENTS

| | | | |
|---|---|---|---|
| 10,975,126 B1 | 4/2021 | Elsayed et al. | |
| 11,479,582 B2 | 10/2022 | Elsayed et al. | |
| 11,939,354 B1 * | 3/2024 | Kandeel ............... | C07K 14/001 |

FOREIGN PATENT DOCUMENTS

WO 2022094139 A1 5/2022

OTHER PUBLICATIONS

A-Geneseq Accession No. BLZ95052 (Dec. 2022), 3 pages (Year: 2022).*
Abouaitah, K., et al., "Nanoformulation Composed of Ellagic Acid and Functionalized Zinc Oxide Nanoparticles Inactivates DNA and RNA Viruses," Pharmaceutics 13, 274, 10.3390/pharmaceutics13122174 (2021), pp. 1-18.
Lawrenz, J., et al., "Severe Acute Respiratory Syndrome Coronavirus 2 Vaccination Boosts Neutralizing Activity Against Seasonal Human Coronaviruses," Clinical Infectious Diseases, 75: pp. e653-e661 (2022).
Xia, S. et al., "Peptide-Based Membrane Fusion Inhibitors Targeting HCoV-229E Spike Protein HR1 and HR2 Domains," Int. J. of Mol. Sci. 19, 487 (2018), pp. 1-15.

* cited by examiner

*Primary Examiner* — Michael Szperka
*Assistant Examiner* — Marianne DiBrino
(74) *Attorney, Agent, or Firm* — Nath, Goldberg & Meyer; Joshua B. Goldberg

(57) ABSTRACT

Fusion peptide inhibitors of human coronavirus 229E are provided. The fusion peptide inhibitors of HCOV-229E include peptide #121

(SEQ ID NO: 2: HVLGDISGINASVVQIQKEIDRLNEVAKNLHESL IYLQE), and peptide

125 (SEQ ID NO: 3: HRLRQIRGIRARVVQIQKEIWRLNEVAKL LNESLIYLQE).

The fusion peptide inhibitors of HCoV-229E may be administered to a subject in need thereof to inhibit or prevent HCOV-229E cellular entry or infection with HCoV-229E. The fusion peptide inhibitors of HCoV-229E may also be used in HCoV-229E inhibition assays.

4 Claims, 1 Drawing Sheet

Specification includes a Sequence Listing.

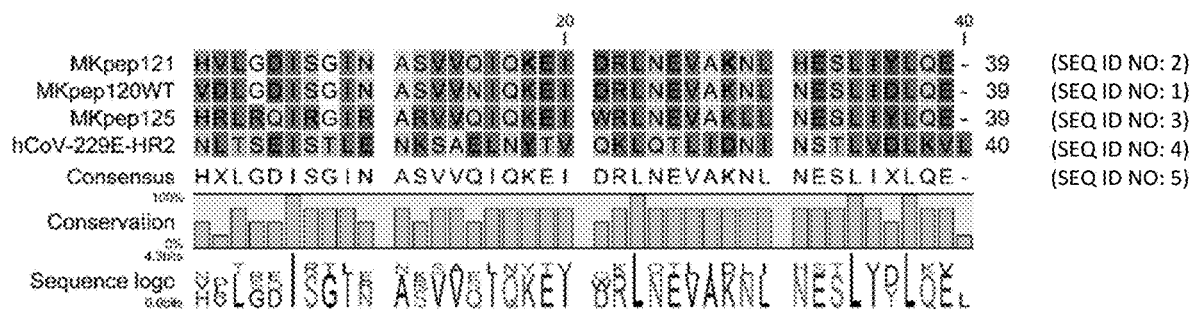

SEQUENCE LISTING

```
Sequence total quantity: 5
SEQ ID NO: 1            moltype = AA  length = 39
FEATURE                 Location/Qualifiers
source                  1..39
                        mol_type = protein
                        organism = Severe acute respiratory syndrome-related
                          coronavirus
SEQUENCE: 1
VDLGDISGIN ASVVNIQKEI DRLNEVAKNL NESLIDLQE                               39

SEQ ID NO: 2            moltype = AA  length = 39
FEATURE                 Location/Qualifiers
source                  1..39
                        mol_type = protein
                        organism = synthetic construct
SEQUENCE: 2
HVLGDISGIN ASVVQIQKEI DRLNEVAKNL HESLIYLQE                               39

SEQ ID NO: 3            moltype = AA  length = 39
FEATURE                 Location/Qualifiers
source                  1..39
                        mol_type = protein
                        organism = synthetic construct
SEQUENCE: 3
HRLRQIRGIR ARVVQIQKEI WRLNEVAKLL NESLIYLQE                               39

SEQ ID NO: 4            moltype = AA  length = 40
FEATURE                 Location/Qualifiers
source                  1..40
                        mol_type = protein
                        organism = Severe acute respiratory syndrome-related
                          coronavirus
SEQUENCE: 4
NLTSEISTLE NKSAELNYTV QKLQTLIDNI NSTLVDLKVL                              40

SEQ ID NO: 5            moltype = AA  length = 39
FEATURE                 Location/Qualifiers
source                  1..39
                        mol_type = protein
                        organism = synthetic construct
VAR_SEQ                 2
                        note = X may equal V, D, R, or L
```

```
VAR_SEQ          36
                 note = X may equal Y or D
SEQUENCE: 5
HXLGDISGIN ASVVQIQKEI DRLNEVAKNL NESLIXLQE                     39
```

FUSION PEPTIDE INHIBITORS OF HUMAN CORONAVIRUS 229E

CROSS-REFERENCE TO RELATED APPLICATION

This application is a divisional of U.S. patent application Ser. No. 18/198,100, filed on May 16, 2023, the entire contents of which are incorporated herein by reference.

INCORPORATION BY REFERENCE OF MATERIAL SUBMITTED IN COMPUTER READABLE FORM

The Applicants hereby incorporate by reference the sequence listing contained in the XML file titled 33102_27U Sequence Listing Update.xml, created May 28, 2023 and having 5,995 bytes of data.

BACKGROUND

1. Field

The disclosure of the present patent application relates to biotechnology, and particularly to fusion peptide inhibitors of human coronavirus 229E ("HCoV-229E") and methods of using said peptides.

2. Description of the Related Art

Coronaviruses (CoVs) are a large family of viruses that can infect both animals and humans. While most CoVs cause mild to moderate respiratory illness in humans, some zoonotic CoVs, such as the severe acute respiratory syndrome coronavirus (SARS-COV), the Middle East respiratory syndrome coronavirus (MERS-COV), and the more recent SARS-COV-2 (the virus that causes COVID-19), can cause severe respiratory illness, leading to epidemics with significant morbidity and mortality.

The four yearly circulating human CoVs (HCoV-229E, HCoV-OC43, HCoV-NL63, and CoV-HKU1) typically cause mild respiratory illness, such as the common cold, in otherwise healthy individuals. These viruses are usually not a cause for serious concern in healthy individuals, but can cause severe illness in immunocompromised individuals, the elderly, and young children.

Some treatments for human coronaviruses have recently been developed. U.S. Pat. No. 10,975,126 B1 teaches MERS-COV inhibitor peptides and their uses. U.S. Pat. No. 11,479,582 B2 teaches SARS-COV-2 inhibitor peptides and their uses. However, currently, there are no approved antiviral treatments specifically targeting HCoV-229E. Symptoms are managed with traditional pain and fever medications, which do not provide any direct treatment for the viral infection.

Thus, fusion peptide inhibitors of HCoV-229E solving the aforementioned problems are desired.

SUMMARY

The fusion peptide inhibitors of HCoV-229E include peptides designed by modification or mutation of previously designed SARS-COV-2 inhibitor peptides. The SARS-CoV inhibitor peptides were designed by modification or mutation of a wild-type SARS-COV fusion protein. The fusion peptide inhibitors of SARS-COV-2 are capable of inhibiting HCoV-229E infection in cells and may be used to prevent and/or treat HCoV-229E infection in a subject in need thereof. The HCoV-229E fusion peptide inhibitors may also be used as reagents for HCoV-229E inhibition assays as a standard or as reference inhibitors.

An embodiment of the present subject matter is directed to methods of inhibiting HCoV-229E infection, preventing HCoV-229E transmission, and/or treating a HCoV-229E infection, including administering to a subject in need thereof a therapeutically effective amount of a pharmaceutical composition comprising one or more HCoV-229E fusion peptide inhibitors. In a further embodiment, the methods of inhibiting HCoV-229E infection may include preventing HCoV-229E infection of a cell.

An embodiment of the present subject matter is directed to methods of using the HCoV-229E fusion peptide inhibitors as reference agents to evaluate inhibition by other candidates against HCoV-229E. These methods may include using the HCOV-229E fusion peptide inhibitors as reference agents in Cell-Cell Fusion Assays, Viral Plaque Formation Assays, Viral RNA Quantitation Assays, or the like.

These and other features of the present subject matter will become readily apparent upon further review of the following specification.

BRIEF DESCRIPTION OF THE DRAWINGS

FIG. 1 depicts an alignment of SARS-COV-2 inhibitor peptides MKpep121 (SEQ ID NO: 2), Mkpep 120WT (SEQ ID NO: 1), and MKpep125 (SEQ ID NO: 3) against the HCoV-229E-HR2 Protein.

Similar reference characters denote corresponding features consistently throughout the attached drawings.

DETAILED DESCRIPTION OF THE PREFERRED EMBODIMENTS

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

The present teachings are directed to the use of fusion peptides that are capable of inhibiting HCoV-229E infection in cells and preventing and/or treating HCoV-229E infection in a subject in need thereof. In this regard, the fusion peptides are capable of use in methods of inhibiting and/or preventing human coronavirus 229E infection of a cell, whether the cell is within or outside of a subject. The fusion peptide inhibitors of HCoV-229E may also be used as reagents for HCoV-229E inhibition assays as a standard or as reference inhibitors.

In an embodiment, the HCoV-229E inhibition assays include a cell-cell fusion assay.

In one embodiment, the present subject matter relates to a method of inhibiting or preventing human coronavirus 229E infection of a cell comprising administering a composition comprising a HCoV-229E fusion peptide inhibitor to the cell. In this regard, the cell can either be within or outside of a subject, patient, or the like. Accordingly, should the cell be within the subject, the present subject matter relates to a method of inhibiting or preventing human coronavirus 229E infection of a cell in a subject comprising administering a composition comprising a HCoV-229E fusion peptide inhibitor to a subject in need thereof.

In certain embodiments, the HCoV-229E fusion peptide inhibitor can comprise a peptide having the amino acid sequence of SEQ ID NO: 2. In other embodiments, the HCoV-229E fusion peptide inhibitor can comprise a peptide having the amino acid sequence of SEQ ID NO: 3. Further contemplated herein are HCoV-229E fusion peptide inhibitor comprising a peptide having the amino acid sequence of SEQ ID NO: 2 and a peptide having the amino acid sequence of SEQ ID NO:3.

Further contemplated herein are pharmaceutical compositions comprising one or more of the fusion peptide inhibitors of HCoV-229E and a pharmaceutically acceptable carrier. Such pharmaceutical compositions may be made using any technique generally known in the art.

As a non-limiting example, a method of making a pharmaceutical composition includes mixing one or more of the fusion peptide inhibitors of HCOV-229E with a pharmaceutically acceptable carrier. For example, the method of making a pharmaceutical composition can include mixing a fusion peptide inhibitor of HCoV-229E under sterile conditions with a pharmaceutically acceptable carrier with preservatives, buffers, and/or propellants to create the pharmaceutical composition.

As a further example, pharmaceutical compositions including fusion peptide inhibitors of HCoV-229E may be made as follows: one or more of the fusion peptide inhibitors of HCoV-229E, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. One or more of the fusion peptide inhibitors of HCoV-229E can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of a fusion peptide inhibitor of HCoV-229E or an amount effective to treat a disease, such as a coronavirus infection, may be determined initially from the Examples described herein and adjusted for specific targeted diseases using routine methods.

An embodiment of the present subject matter is directed to compositions including one or more of the fusion peptide inhibitors of HCoV-229E and one or more expression systems. The expression system may be a viral-based expression system, a plasmid-based expression system, or any other expression system suitable for causing or enhancing expression of the fusion peptide inhibitors of HCoV-229E in a bacterium, yeast, or mammalian cell. The expression system may include a promoter sequence and DNA or RNA encoding one or more of the fusion peptide inhibitors of HCOV-229E.

In certain embodiments, the present pharmaceutical composition can comprise a HCoV-229E fusion peptide inhibitor comprising a peptide having the amino acid sequence of SEQ ID NO: 2. In other embodiments, the present pharmaceutical composition can comprise a HCoV-229E fusion peptide inhibitor comprising a peptide having the amino acid sequence of SEQ ID NO: 3. Further contemplated herein pharmaceutical compositions that can comprise a HCoV-229E fusion peptide inhibitor comprising a peptide having the amino acid sequence of SEQ ID NO: 2 and a peptide having the amino acid sequence of SEQ ID NO:3.

An embodiment of the present subject matter is directed to methods of using the fusion peptide inhibitors of HCoV-229E as reference agents to evaluate inhibition by other candidates against HCoV-229E. These methods may include using the fusion peptide inhibitors of HCoV-229E as reference agents in Cell-Cell Fusion Assays, Viral Plaque Formation Assays, Viral RNA Quantitation Assays, or the like.

The fusion peptide inhibitors of HCoV-229E can be administered to a subject in need thereof. In an embodiment, the fusion peptide inhibitors of HCOV-229E can be administered to a subject in need thereof to inhibit HCoV-229E infection, prevent HCoV-229E transmission, and/or treat a HCoV-229E infection.

An embodiment of the present subject matter is directed to a method of inhibiting HCoV-229E infection, preventing HCoV-229E transmission, and/or treating a HCoV-229E infection, comprising administering to a subject in need thereof a therapeutically effective amount of the pharmaceutical composition according to the present subject matter.

The fusion peptide inhibitors of HCoV-229E or pharmaceutical compositions thereof can be administered to a subject by any suitable route. For example, the compositions can be administered nasally, rectally, intracisternally, intraperitoneally, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The CoV genome encodes four structural proteins: spike (S), membrane (M), envelope (E), and nucleocapsid (N). Viral membrane fusion is an essential step of virus replication, which is accomplished by the viral spike and leads to the fusion of the viral and cell membranes. The CoV S protein is composed of two subunits, S1 and S2. S1 binds the host cell ACE2 receptor. Cleavage of S1 by host cell proteases exposes a highly hydrophobic membrane-binding domain of the S2 subunit. The S2 subunit contains two domains, heptad repeat domain 1 (HR1) and heptad repeat domain 2 (HR2). HR1 forms a homotrimer exposing three hydrophobic pockets on its surface, which host the HR2 domain during the active fusion process. An HR domain is composed of tandem repeat motifs of seven residues (named a-g). Of the seven residues, the first (a) and fourth (d) are predominantly hydrophobic or bulky.

The fusion peptide inhibitors of HCoV-229E are designed by modification or mutation of a surface structure protein of SARS-COV-2 in the virus S2 spike region. The heptad repeat regions (HR1 and HR2) of S2 interact to help in fusion of SARS-COV-2 with cell membranes. The SARS-COV-2 inhibitor peptide S2 HR2 derivatives were optimized to interfere with the proper mechanism of HR1-HR2 interactions.

In an embodiment, the fusion peptide inhibitors of HCoV-229E include peptide

121 (SEQ ID NO: 2: HVLGDISGINASVVQIQKEIDRLNEVAKN LHESLIYLQE), peptide

125 (SEQ ID NO: 3: HRLRQIRGIRARVVQIQKEIWRLNEVAKL LNESLIYLQE), or a combination thereof.

In an embodiment, the method of using the HCoV-229E fusion peptide inhibitors as reference agents to evaluate inhibition by other candidates against HCoV-229E includes providing at least one HCoV-229E fusion peptide inhibitor and at least one candidate inhibitor, assaying HCoV-229E fusion in the presence of the at least one HCoV-229E fusion peptide inhibitor, assaying HCoV-229E fusion in the presence of the at least one candidate inhibitor, and comparing the results for the HCoV-229E fusion peptide inhibitor to the results for the at least one candidate inhibitor. These methods may further include using the HCoV-229E fusion peptide inhibitors as reference agents in Cell-Cell Fusion Assays, Viral Plaque Formation Assays, Viral RNA Quantitation Assays, or the like.

The following examples illustrate the present subject matter.

Example 1

Designing Peptide Inhibitors of HCoV-229E

To test the possible extended-spectrum efficacy, the sequences of previously developed SARSS-COV inhibitor peptides #121 and #125 (See U.S. Pat. No. 11,479,582 and Table 1) were matched with the HCoV-229E-HR2 protein (See FIG. 1). Several residues were discovered to be highly conserved. The helical component, made up of hydrophobic residues, was also constant among the analysed peptide sequences; variations among the sequences were most pronounced for the hydrophilic residues. The interface acids between the fusion core proteins HR1 and HR2 were also highly conserved in the SARS-COV-2 inhibitor peptides and hCoV-229E-HR2. This discovery laid the groundwork for further exploration of the broader spectrum of peptides #121 and #125 for hCoV-229E inhibition. These peptide sequences are shown in Table 1, with mutated residues highlighted in bold.

TABLE 1

Peptide Sequences

| Name | Peptide Sequence | SEQ ID |
|---|---|---|
| Peptide 120 (WT) | VDLGDISGINASVVNIQKEIDRLNEV AKNLNESLIDLQE | SEQ ID NO: 1 |
| Peptide 121 | HVLGDISGINASVVQIQKEIDRLNEV AKNLHESLIYLQE | SEQ ID NO: 2 |
| Peptide 125 | HRLRQIRGIRARVVQIQKEIWRLNEV AKLLNESLIYLQE | SEQ ID NO: 3 |

To get insights into the calculated values of similarity and differences between peptides #121 and #125 and hCoV-229E-HR2, pairwise sequence comparison statistics were calculated (Table 2). The analysis in FIG. 1 showed only one sequence gap allocated in the hCoV-229E-HR sequence and 32-35 different residues. However, most of these differences comprise residues of similar functional or structural aspects. The results of this analysis are presented in Table 2, with the upper diagonal panel showing the number of gaps and the lower diagonal panel showing the number of differences.

TABLE 2

| Pairwise Comparison Statistics | | | | | |
|---|---|---|---|---|---|
| | | 1 | 2 | 3 | 4 |
| Peptide 121 | 1 | | 0 | 0 | 1 |
| MKpep120WT | 2 | 5 | | 0 | 1 |
| Peptide 125 | 3 | 9 | 11 | | 1 |
| HCoV-229E-HR2 | 4 | 34 | 32 | 35 | |

Example 2

Antiviral Assay

A plaque reduction test was performed as previously reported (AbouAitah, K., et al., "Nanoformulation Composed of Ellagic Acid and Functionalized Zinc Oxide Nanoparticles Inactivates DNA and RNA Viruses," Pharmaceutics 13, 274, 10.3390/pharmaceutics 13122174 (2021)). Vero E6 cells were grown on a six-well plate for 24 hours at 37° C. In parallel to the untreated viral control, the virus was incubated for 30 minutes with various dilutions of the peptides. The cells were injected with (100 µl/well) countable virus/sample mixes after the growth media was withdrawn from the cell culture plates. After 1 hour of virus adsorption, 1.5 ml of DMEM supplemented with 2% agarose was added to the cell monolayer; plates were allowed to harden and incubated at 37° C. for 3 days. Formalin 10% was applied to the plates for two hours before staining with 0.1 percent crystal violet in distilled water. Untreated virus was incubated with Vero E6 cells in control wells, and plaques were enumerated. The decrease in plaque formation in comparison to control wells was calculated using Formula 1:

$$\% \text{ inhibition} = \frac{\text{viral count(untreated)} - \text{viral count(treated)}}{\text{viral count(untreated)}} \quad \text{Formula 1}$$

Peptides 121 and 125 demonstrated inhibition of HCoV-229E with the peptides having a selectivity index of 13.06 and 17.56, respectively. (See Table 3)

TABLE 3

Inhibitory Properties of Tested Peptides Against HCoV-229E

| Peptide # | CC50 µM | IC50 µM | Selectivity Index |
|---|---|---|---|
| Peptide 121 | 250.773 | 14.1979 | 13.06 |
| Peptide 125 | 255.221 | 14.537 | 17.56 |

It is to be understood that the fusion peptide inhibitors of human coronavirus 229E are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

---

I claim:

1. A pharmaceutical composition comprising a HCoV-229E fusion peptide inhibitor and a pharmaceutically acceptable carrier; wherein the HCoV-229E fusion peptide inhibitor consists of a peptide selected from the group consisting of a peptide consisting of the amino acid sequence of SEQ ID NO: 2, a peptide consisting of the amino acid sequence of SEQ ID NO: 3, and a combination thereof.

2. The pharmaceutical composition of claim 1, wherein the HCoV-229E fusion peptide inhibitor consists of a peptide consisting of the amino acid sequence of SEQ ID NO: 2.

3. The pharmaceutical composition of claim 1, wherein the HCoV-229E fusion peptide inhibitor consists of a peptide consisting of the amino acid sequence of SEQ ID NO: 3.

4. The pharmaceutical composition of claim 1, wherein the HCoV-229E fusion peptide inhibitor consists of a peptide consisting of the amino acid sequence of SEQ ID NO: 2 and a peptide consist ng of having the amino acid sequence of SEQ ID NO:3.

* * * * *